United States Patent [19]

Nagy

[11] Patent Number: 5,291,894
[45] Date of Patent: Mar. 8, 1994

[54] APPARATUS FOR TREATING A PATIENT WITH ACOUSTIC WAVES

[76] Inventor: Lajos Z. Nagy, Groot Hertoginnelaan 26, 1405 Ed Bussum, Netherlands

[21] Appl. No.: 886,437

[22] Filed: May 20, 1992

Related U.S. Application Data

[63] Continuation-in-part of Ser. No. 602,513, Oct. 24, 1990, abandoned.

[30] Foreign Application Priority Data

Nov. 14, 1989 [NL] Netherlands .................. 8902809

[51] Int. Cl.$^5$ ............................................ A61H 23/00
[52] U.S. Cl. ............................... 128/670; 128/732; 607/97
[58] Field of Search .............. 128/700, 660.01, 660.02, 128/420.5, 905; 600/13, 27, 28, 26

[56] References Cited

U.S. PATENT DOCUMENTS

| | | | |
|---|---|---|---|
| 4,184,485 | 1/1980 | Agoston | 128/905 |
| 4,538,596 | 9/1985 | Colasante | 128/32 |
| 4,556,070 | 12/1985 | Vanguine et al. | 128/804 |
| 4,576,178 | 3/1986 | Johnson | 128/700 |
| 4,802,486 | 2/1989 | Goodman et al. | 128/633 |
| 4,811,742 | 3/1989 | Hassel et al. | 128/733 |
| 4,969,459 | 11/1990 | Gusakov | 128/399 |
| 5,024,235 | 6/1991 | Ayers | 128/905 |

FOREIGN PATENT DOCUMENTS

| | | |
|---|---|---|
| 0112082 | 6/1984 | European Pat. Off. |
| WO8503634 | 8/1985 | PCT Int'l Appl. |
| 1286016 | 8/1972 | United Kingdom |

*Primary Examiner*—William E. Kamm
*Assistant Examiner*—Scott M. Getzow
*Attorney, Agent, or Firm*—Lorusso & Loud

[57] ABSTRACT

An apparatus for treating a patient with acoustic waves having a treatment head with a treatment head which is connectable to a generator with variable frequency. The apparatus has at least a first sensor which measures the heart rate of the patient before and after treatment, wherein the frequency of the generator is adjustable in dependence on the change of the heart rate as a result of treatment.

15 Claims, 1 Drawing Sheet

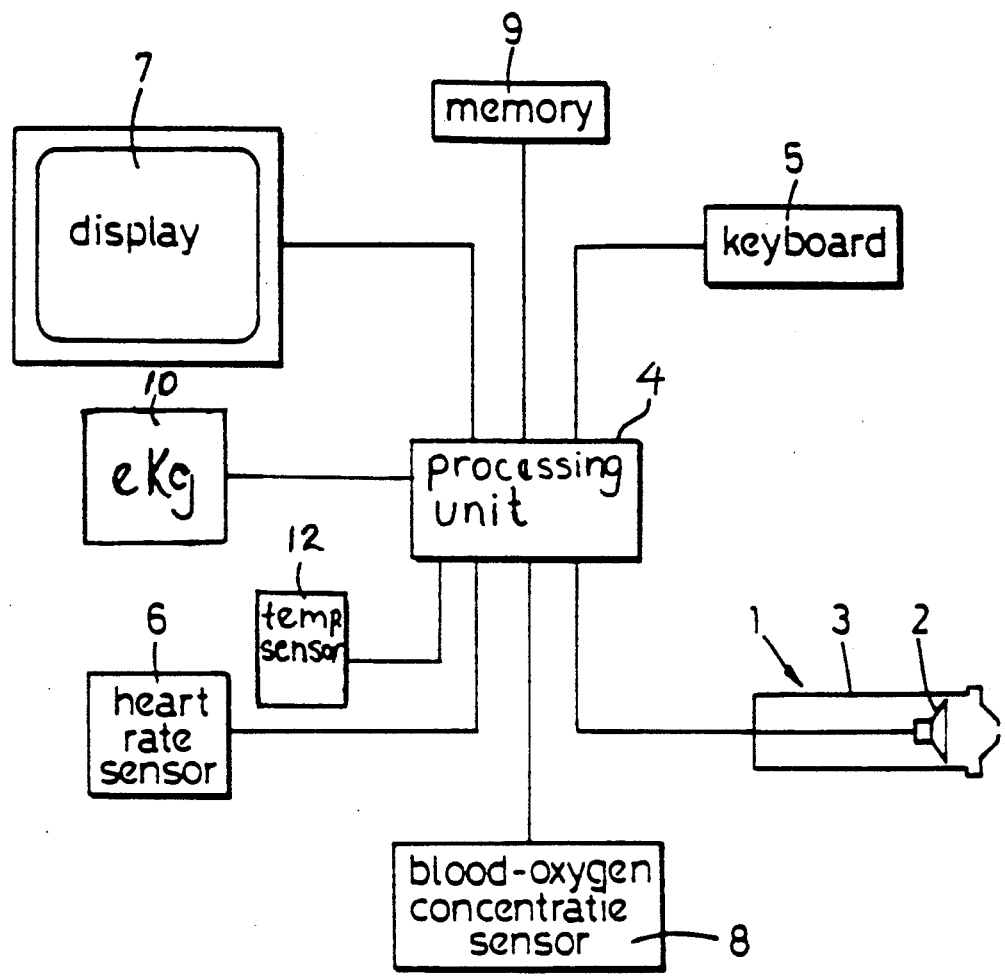

APPARATUS FOR TREATING A PATIENT WITH ACOUSTIC WAVES

This is a continuation-in-part of copending application(s) 07/602,513 filed on Oct. 24, 1990 now abandoned.

BACKGROUND OF THE INVENTION

This invention relates to an apparatus for treating a patient with acoustic and/or electromagnetic waves or mechanical vibrations, comprising a treatment head with a source for providing acoustic and/or electromagnetic waves or mechanical vibrations which is connectable to a generator with a variable frequency, and at least one sensor for measuring a parameter of the patient.

The apparatus of the invention is intended for the therapeutic treatment of disturbances in the blood circulation, especially of obstructions or stenosis occurring in the limbs of the patient or of body parts which are insufficiently provided with blood for other reasons. Treatment has been effective when the patient feels warmth at the treated body part or by an increase of the temperature measured by a thermometer. A thermometer can be used which is located against or immediately adjacent the treated body part for measuring the temperature.

SUMMARY OF THE INVENTION

The invention aims to provide an apparatus of the above-mentioned type, with which said disturbances in the blood circulation can be treated with an increased effectiveness.

The invention is based on the insight that the effectiveness of the treatment can not only be determined by measuring the temperature but in a more efficient manner also by means of other parameters of the patient.

In order to improve the effectiveness of the treatment, the invention generally provides an apparatus of this type further comprising a first sensor for measuring the heart rate of the patient before and after the treatment, wherein the frequency of the generator is adjustable in dependence on the change of the heart rate a a result of the treatment.

Experiments of the applicant have shown that by measuring the change of the heart rate as a result of the treatment, the frequency of the generator can adjusted in such a manner that a very effective next treatment becomes possible. When monitoring the patient during treatment, it is preferred to measure the heart rate during the treatment as well.

It has further been found that a more accurate measurement of the temperature change occurs when the temperature is measured at several locations on the peripheral ends of the arms or legs of the patient. Accordingly, a favorable embodiment of the apparatus according to the invention, a plurality, preferably six, temperature sensors are provided. The temperature sensors can be disposed on the peripheral ends of the arms or legs of the patient, wherein the frequency of the generator is adjustable in dependence on the temperature changes as a result of the treatment.

Experiments have further shown that the oxygen concentration in the blood of the patient is affected by the treatment. According to the invention it is therefore advantageous to provide a sensor for measuring the oxygen concentration in the blood of the patient, wherein the frequency of the generator is adjustable in dependence on the change of the oxygen concentration as a result of the treatment.

According to the invention, it is possible that the generator is made as a signal generator for generating signals with any desired wave shape and frequency. It has been found that depending on the type of the affection or complaint to be treated, treatment with different wave shapes and frequencies result in an increased effectiveness of the treatment. The wave shape my be, for example, a sine wave, a square wave or a saw tooth wave.

According to a preferred embodiment of the invention, the treatment head and each sensor capable of sensing the physiological parameters of heart rate, electrocardiogram response, temperature and blood-oxygen level, are connected to a processing unit which controls the treatment head and processes the measuring signals of the sensor(s) and displays these signals on a display screen, wherein the signal shape and frequency are adjustable through a keyboard.

Thereby the treatment and measurement of the different parameters may occur in an advantageous manner as controlled by a processing unit preferably comprising a microprocessor.

BRIEF DESCRIPTION OF THE DRAWING

The invention will be further explained by reference to the drawing in which an embodiment of the apparatus according to the invention is shown in a simplified block diagram.

DETAILED DESCRIPTION OF THE PREFERRED EMBODIMENT

The apparatus shown for treating a patient with acoustic waves comprises a treatment head 1 with an acoustic wave source 2. In the embodiment shown, the acoustic wave source 2 is made as a loudspeaker and is mounted within a cylindrical housing 3. As an alternative, the acoustic wave source 2 can be mounted on the outside of the cylindrical housing 3 of the treatment head 1 of the described apparatus. It is further noted that instead of a loudspeaker as an acoustic wave source 2, it is also possible to use other types of acoustic wave sources. Further, a source of electromagnetic waves can be used instead of an acoustic wave source 2. Moreover, a source providing mechanical vibrations can be used as an alternative. For example, a piezo-electric element can be used as a mechanical vibration source. The treatment head 1 is connected to a processing unit 4 which includes a signal generator not further shown. The generator can generate signals with any desired wave shape and frequency. The signal generator may have several different embodiments. For example, the signal generator may be a programmable frequency generator which contains a dual twelve bit digital to analog converter for setting the exact frequency in very small steps. Any signal generator known in the art that is capable of providing a signal with variable frequency and variable wave shape is acceptable.

The signals generated by the signal generator are supplied to the acoustic wave source 2 of the treatment head 1. Although for the treatment of many affections of the vein system disturbing the blood circulation, generally a signal with a frequency between 20 Hz and 1000 Hz is used, higher frequencies up to ultrasonic frequency may be used. Generally, acoustic waves with a frequency range of 20 Hz up to 20,000 Hz may be used. Additionally, ultrasonic waves, up to a frequency of 40,000 Hz are effective. Besides square waves, it is further possible to use other signal shapes such as more or less sinusoidal signals.

The processing unit 4 can operate in two different fashions. In one embodiment, the processing unit 4 controls the treatment head 1 and determines the time during which the body part of the patient is treated with the acoustic waves. In this embodiment, the processing unit 4 determines the intensity of the acoustic waves. In a second embodiment, the desired intensity and treatment time can, for example, be supplied to the processing unit 4 through a keyboard 5 by a medical attendant. In this embodiment, the processing unit 4 simply switches the treatment head 1 on and off.

The medical attendant can determine the different adjustments in accordance with his expertise by means of the results of a previous treatment. Observations have shown that the effectiveness of a treatment can be determined by means of the heart rate of the patient. The heart rate parameter most helpful is heart rate stability.

Many patients with blood circulation problems show a very irregular heart rate. For example, a patient with a heart rate of sixty beats per minute, a heart beat can be measured at the first second, while the second heart beat does not occur until the third second, where two successive heart beats may occur.

For measuring this heart rate, a sensor 6 is provided which supplies a measuring signal to the processing unit 4. The heart rate is measured during a predetermined measuring time before the treatment and during a predetermined measuring time after the treatment. By these measurements, a comparison of the heart rate before and after treatment can be made. If, after comparison, the stability of the heart rate has increased, it is likely that the treatment has been effective. The next treatment will then be made with the same settings for treatment time, intensity, frequency and wave shape. If, however, the stability of the heart rate did not increase, the treatment has not been effective and the next treatment will be made with a different setting on on of the above-mentioned parameters.

As a general rule, each of the above-mentioned settings will be changed in succession at each next treatment if the comparison shows that the stability of the heart rate did not increase as follows:
1. Longer treatment time.
2. Higher intensity.
3. Higher frequency.
4. Different wave shape.

The measuring results obtained can, for example, be shown on a display screen 7 or in another suitable manner. It is preferred to continuously measure the heart rate during a treatment so that the patient is monitored during the treatment.

As an alternative, the sensor 6 may be replaced by an electrocardiogram sensor 10 adapted to measure the electrocardiogram (ECG) of the patient so that the processing unit 4 can display the ECG before and after treatment. The wave shape measured generally shows a plurality of high and low values which are indicated in the art as PQRS. The P-wave is the electrical activity resulting in the contraction of both atriums of the heart. The QRS complex is the electrical activity of the ventricles of the heart.

The medical attendant can determine the effectiveness of the treatment by means of the difference between the ECG before and after treatment. By comparing the PQRS wave shape of the heart beat, it is first possible to determine the heart rate and thereby the stability of the heart rate as described above. Moreover, the amplitude of the PQRS wave shape can be compared before and after treatment. If the amplitude has increased, this is an indication of an effective treatment.

Further, the temperature of the treated body part, in particular at the peripheral end thereof is of importance. To this end, several temperature sensors 12 are provided, preferably six, which for example, in the case of treating the leg of a patient, can be disposed on three different locations on both feet of the patient. The temperature is continuously measured starting at a time before the treatment until several minutes after the treatment so that the temperature is monitored and the temperatures before and after treatment can be compared to determine the effectiveness of the treatment. A temperature increase of 0.3° C. to 1.0° C. is an indication of an effective treatment. Experiments have shown that with patients having serious blood circulation problems, a temperature increase of 6° C. may be measured. Again, if a temperature increase is not measured, the above-explained changes of the settings will be made at the next treatment.

The invention may provide a sensor 8 for measuring the oxygen concentration in the blood. It has been found that the oxygen concentration in the blood is also changed as a result of the treatment of the patient.

All measuring data can be shown in a suitable manner on the display screen 7, where, in particular, the change as a result of the treatment is of importance. The medical attendant can determine the treatment time, intensity, frequency and signal shape through the keyboard for a next treatment. All data relating to a certain patient with respect to the treatment can be stored in a memory 9. The processing unit 4 can generally comprise a microcomputer with suitable interface circuits for connecting the treatment head 1 and heart rate sensor 6 and the optional blood-oxygen sensor 8. The processing unit 4 processes the measuring signals provided by the sensor or sensors used. By comparing the measuring signals obtained before and after a treatment, the medical attendant can determine effectiveness of the treatment. If the treatment has been effective, the microcomputer stores in the memory 9 that the next treatment of the respective patient should be made with the same settings of the treatment signal.

If the treatment has not been effective, the microcomputer stores in the memory 9 a change of the setting of one of the parameters of the treatment signal. At the next treatment, the medical attendant only has to introduce the name of the patient and the microcomputer automatically makes all settings of the treatment signals. Introducing the name of a patient may, for example, occur by inserting a floppy disk containing all information required for that patient. Each patient may have its own floppy disk containing all treatment data, should patient data be stored in this fashion.

As an alternative, the required settings may of course be made manually by the medical attendant.

By way of example, it should be noted that in using temperature sensors 12, the treatment should result in a temperature increase in view of an improved blood circulation. By comparing the temperature before and after treatment, the medical attendant can determine if the treatment has been effective or not. If the temperature has increased, the next treatment may take place with the same settings of the parameters of the acoustic wave signal and length of the treatment. However, if the temperature measurement shows no significant temperature change, the medical attendant will change the setting of one or more of these parameters and/or the length of the treatment for a next treatment of the patient.

As the therapeutic treatment of patients with disturbances in the blood circulation requires a number of subsequent treatments, the effectiveness of each subsequent treatment can be improved significantly so that the overall therapeutic treatment can be very successful.

It is also possible to connect the processing unit 4 through suitable means to a central computer, to which a plurality of processing units 4 can be connected and in which all data is stored centrally. Further, this central computer may provide adjustment data to the processing units 4. This connection to a central computer can be made through any well known local area network or the like.

It will be understood that many additional changes in the details, materials, steps and arrangement of parts, which have been herein described and illustrated in order to explain the nature of the invention, may be used by those skilled in the art within the principles and scope of the invention as expressed in the appended claims.

Having thus described our invention, what we claim as new and desire to secure by Letters Patent of the United States is:

1. An apparatus for treating a patient for blood circulation disturbances with a treatment of one of; acoustic waves, electromagnetic waves, or a combination of acoustic waves and electromagnetic waves, comprising:
   a processing unit having means for generating a variable frequency in dependence on the change of the heart rate as a result of said treatment;
   a treatment head having means for providing acoustic and/or electromagnetic waves, said treatment head coupled with said means for generating a variable frequency within a range specific to treating disturbances in blood circulation;
   a plurality of sensors in communication with said processing unit each sensor having means for transmitting signals indicative of a physiological measurement, said plurality of sensors including a heart rate sensor having means for measuring the heart rate of said patient before and after said treatment, said processing unit having, means for controlling said treatment head and means for processing said signals transmitted by said sensors;
   a display screen in communication with said processing unit that displays said signals on said display screen; and
   a keyboard in communication with said processing unit having means for adjusting said variable frequency.

2. An apparatus according to claim 1, wherein said plurality of sensors further includes at least one temperature sensor which can be disposed on the peripheral ends of the arms or legs of said patient so that said variable frequency of said generator is adjustable in dependence on temperature changes of said patient as a result of treatment.

3. An apparatus according to claim 1 wherein said plurality of sensors includes at least one sensor having means for measuring the electrocardiogram of the patient.

4. An apparatus according to claim 1, wherein said range specific to treating disturbances in blood circulation, is from 20 Hz up to 20,000 Hz.

5. An apparatus according to claim 1, wherein said plurality of sensors includes at least one sensor for measuring the temperature of the patient.

6. An apparatus according to claim 1, wherein said plurality of sensors includes at least one sensor for measuring the blood-oxygen level of the patient.

7. An apparatus according to claim 1, said keyboard further including means for adjusting treatment time.

8. An apparatus according to claim 1, said keyboard further including means for adjusting a waves shape of said waves.

9. An apparatus for treating a patient for blood circulation disturbances with a treatment of acoustic waves, electromagnetic waves, or both, comprising:
   a microprocessor including means for generating signals, said signals having a variable frequency and wave shape, said microprocessor having means for receiving at least one of the following inputs; length of said treatment, intensity of said treatment, a desired frequency of said signals and a desired waveshape of said signals, said microprocessor further comprising means for adjusting the values of said inputs,
   a treatment head adapted to receive said signals from said means for generating signals, said treatment head having means for administering acoustic and/or electromagnetic waves of a frequency specific to improving blood circulation in a patient,
   means for sensing at least one physiological parameter before and after said treatment, said means for sensing including means for outputting measuring signals representative of said at least one physiological parameter before and after treatment, said measuring signals indicating the need for adjustment of said values of said inputs.

10. An apparatus according to claim 9, said at least one physiological parameter includes heart rate.

11. An apparatus according to claim 9, said at least one physiological parameter including body temperature.

12. An apparatus according to claim 9, said at least one physiological parameter including blood-oxygen level.

13. An apparatus according to claim 9, said at least one physiological parameter including an EKG.

14. An apparatus according to claim 9, said means for outputting comprising a display.

15. An apparatus according to claim 9, said means for adjusting the values of said inputs comprising a keyboard.

* * * * *